(12) United States Patent
Plate et al.

(10) Patent No.: US 11,426,535 B2
(45) Date of Patent: Aug. 30, 2022

(54) INTRAVENOUS FLUID WARMER USING UNIFORM THERMAL FIELD

(71) Applicant: Enthermics Medical Systems, Inc., Menomonee Falls, WI (US)

(72) Inventors: Jeffrey Plate, Brookfield, WI (US); Paul Martis, Grafton, WI (US)

(73) Assignee: Enthermics Medical Systems, Inc., Menomonee Falls, WI (US)

( * ) Notice: Subject to any disclaimer, the term of this patent is extended or adjusted under 35 U.S.C. 154(b) by 23 days.

(21) Appl. No.: 16/871,208

(22) Filed: May 11, 2020

(65) Prior Publication Data

US 2020/0353178 A1 Nov. 12, 2020

Related U.S. Application Data

(60) Provisional application No. 62/845,978, filed on May 10, 2019.

(51) Int. Cl.
*A61M 5/44* (2006.01)
*A61J 1/12* (2006.01)
*A61J 1/16* (2006.01)

(52) U.S. Cl.
CPC .......... *A61M 5/44* (2013.01); *A61J 1/12* (2013.01); *A61J 1/16* (2013.01); *A61M 2205/3368* (2013.01); *A61M 2205/362* (2013.01)

(58) Field of Classification Search
CPC .............. A61M 2205/587; A61M 5/44; A61M 2205/3368; A61M 2205/362; A61M 5/445; A61J 1/10; A61J 1/12; A61J 1/06; A61J 1/18; A61J 1/16; A61B 2050/105; A61B 50/10; A61B 50/13; A61B 2050/185

See application file for complete search history.

(56) References Cited

U.S. PATENT DOCUMENTS

| | | | |
|---|---|---|---|
| 3,839,622 A | 10/1974 | Mastin | |
| 6,384,380 B1 | 5/2002 | Faries, Jr. et al. | |
| 6,660,974 B2 | 12/2003 | Faries, Jr. et al. | |
| 9,656,029 B2 | 5/2017 | Tsang et al. | |
| 2004/0247016 A1* | 12/2004 | Faries, Jr. | A61B 50/13 374/162 |
| 2010/0276411 A1* | 11/2010 | Hansen | A61M 5/44 219/385 |
| 2017/0281879 A1* | 10/2017 | Shimel | A61M 5/445 |

* cited by examiner

*Primary Examiner* — Amber R Stiles
*Assistant Examiner* — Avery Smale
(74) *Attorney, Agent, or Firm* — Boyle Fredrickson S.C.

(57) ABSTRACT

A heating cabinet for IV bags provides a uniform thermal field promoted by circulated heated air passing through air permeable shelves. Temperatures of the IV bags are modeled through a knowledge of a temperature of the uniform thermal field and arrival time of the IV bags eliminating a need for separate temperature sensors and control loops. Bag status may be signaled through modulated light distinguishable by individuals with limited color sensitivity. Signals are associated with particular IV bags by projecting the light of the signals into the IV bags themselves.

20 Claims, 2 Drawing Sheets

INTRAVENOUS FLUID WARMER USING UNIFORM THERMAL FIELD

CROSS REFERENCE TO RELATED APPLICATION

This application claims the benefit of U.S. Provisional Application No. 62/845,978, filed May 10, 2019, and hereby incorporated by reference.

STATEMENT REGARDING FEDERALLY SPONSORED RESEARCH OR DEVELOPMENT

BACKGROUND OF THE INVENTION

The present invention relates to an apparatus for heating intravenous fluid (IV bags) and in particular to an improved heating system using a uniform thermal field.

During medical care, it may be necessary to introduce a fluid into a human body intravenously. Such fluids, including, for example, blood, saline solution, antibiotic solution, and the like, may be stored in flexible IV bags. These IV bags are normally kept at room temperature before use and are warmed for introduction into the patient to prevent patient discomfort and undesired reduction in patient body temperature.

It is known to produce IV bag heating cabinets having multiple compartments each of which may receive an individual IV bag. Compartments may each have a heater and temperature sensor to be individually thermostatically controlled to bring individual IV bags quickly to a desired temperature (close to body temperature). The heaters may heat a shelf having a trough shape promoting contact between the IV bag and the shelf and warming the IV bag through conduction.

An alternative approach may be to have a single compartment which incorporates a container for placing multiple IV bags to be warmed. This approach can make organizing the IV bags, to support a first-in/first-out process, difficult. This may result in extra time and effort for the user to sort IV bags in the container, IV bags to be warmed longer than specified and have to be disposed of, or infusion of IV solution that has not warmed sufficiently to provide the intended effect.

The nature of medical practices is such that IV bags may be required on short notice, making it desirable that IV bags be quickly brought to the desired temperature. Rapid heating of the significant thermal mass of an IV bag can be difficult, requiring high wattage heating elements together with accurate monitoring of IV fluid temperature to prevent damage from overheating. Measurement of the temperature of the IV fluid is difficult. In order to preserve the sterile field of the IV bag, temperature of the fluid must be sensed from outside of the bag since it must be made outside of the bag and is subject to errors caused by uneven heat distribution within the IV fluid.

SUMMARY OF THE INVENTION

The present inventors have recognized that robust IV bag heating can be obtained by providing a uniform heat field throughout the warming cabinet using forced air circulation and shared high wattage heaters eliminating the need for high wattage heaters in each compartment. The heat field may be regulated globally to the desired temperature of the IV bags preventing temperature extremes that can occur with local heaters when there is a lag in sensing IV bag temperature. The uniform heat field heats the bags from all sides reducing temperature stratification, better enabling the temperature of the bags to be determined by a modeling process that eliminates the problems of temperature sensing through the IV bag and the cost of multiple temperature sensors and controllers.

In one embodiment, the invention provides a warming cabinet for IV bags holding liquid medicament and having a housing providing a heating cavity with a door movable between a closed state covering the heating cavity and an open state allowing access to the heating cavity. A blower circulates air through the heating cavity, and a set of shelves divides the heating cavity into compartments each sized to receive an IV bag to be warmed and each compartment providing air passageways there between to receive the circulated air along paths through multiple compartments. An electrical heater is positioned within the circulated air for heating the same, and a control unit controls the heater to provide a temperature of the circulated air equal to a desired temperature of the medical products in the compartments. A control unit controls the electrical heater and executes a stored program to model the temperature of the IV bags and, based on that modeling, indicate particular IV bags that are warmed and ready for use.

It is thus a feature of at least one embodiment of the invention to provide a simple and reliable method of heating IV bags without overheating the IV bags by establishing a uniform thermal field which naturally brings the IV bags to the desired temperature. The fan produces a forced convection enforcing a uniform thermal field around each IV bag with minimal influence from local cooling by newly introduced IV bags.

By modeling the temperature rise of the bags, problems of monitoring IV bag temperature for local thermostatic control are eliminated. The heating model may then be used to extrapolate the temperature of the fluid within the IV bag during the warming cycle. The heating model may be time dependent, simply counting the elapsed time the IV bag has been in the warmer, pausing when environmental factors such as door opening may cause delayed heating. Or the model may be a more complex calculation, measuring differences in air and fluid temperature to use Newton's Law of Cooling in deriving the fluid temperature with the goal of compensating for environmental factors and daily use, such as restocking with ambient temperature IV bags.

The control unit may control the circulated air temperature to the temperature of the human body plus or minus 5 degrees Fahrenheit.

It is thus a feature of at least one embodiment of the invention to eliminate risk of exposure of the IV bags to over-temperature such as can occur with local conductive heaters under slowly responding temperature sensing.

The electrical heater may communicate with the IV bags primarily through convection of the circulated air rather than conduction.

It is thus a feature of at least one embodiment of the invention to provide a moderating thermal reservoir in the form of the convected air providing a thermal reserve for rapidly heating newly introduced bags without the need for high wattage individual heaters.

The shelves may include a plurality of openings allowing air passage through IV bag-supporting surfaces of the shelves. In some embodiments the holes may comprise at least 20 percent of the shelf area and the shelves may be larger in area than the resting area of the IV bags by at least 25 percent.

It is thus a feature of at least one embodiment of the invention to ensure ample airflow paths around the bag so that they may be heated from all sides rather than from a single surface as is done with conductive heaters. It is another feature of this embodiment to preserve good airflow attendant to producing a uniform thermal field.

The warming cabinet may include a manifold for distributing air from the fan to each compartment, wherein the manifold provides vertical channels extending to the sides of the compartments and passing along the heater surface.

It is thus a feature of at least one embodiment of the invention to promote consistency of airflow under a variety of different loadings of the compartments with IV bags.

The warming cabinet may provide proximity sensors associated with each compartment detecting the presence of an IV bag in that compartment and the compartments may be arranged in at least two columns separated by a central divider and wherein the proximity sensors are positioned in the central divider to face outward therefrom.

It is thus a feature of at least one embodiment of the invention to provide a simple method of positioning the proximity sensors and interconnecting wiring associated with each individual compartment.

The warming cabinet may further include indicator lamps associated with each compartment for indicating a state of the IV bag with respect to its heating wherein the states include a state indicating that the IV bag is heating and not at temperature and a state indicating that the IV bag is at the desired temperature.

It is thus a feature of at least one embodiment of the invention to both indicate whether the bags are ready and indicate that the bags have been properly sensed for monitoring by the controller.

The warming cabinet may include indicator lamps to denote the state indicating that the IV bag is heating and not at temperature by a predetermined first intensity modulation of the indicator lamp changing the intensity of the lamp and to denote the state indicating that the IV bag is at the desired temperature with a steady illumination of the indicator lamp.

It is thus a feature of at least one embodiment of the invention to provide an intuitive indication of the state of the IV bags that can be recognized at a distance and which does not require color cues that may be misinterpreted by those without full color vision.

The intensity modulation provides a continuous variation in intensity.

It is thus a feature of at least one embodiment of the invention to provide a signal that intuitively shows a gradual action of heating.

The indicator lamps may further indicate a state indicating that the IV bag is at temperature and should be used next.

It is thus a feature of at least one embodiment of the invention to provide a ranking of IV bags with respect to use to minimize average IV bag heating such as can, over time, degrade the IV material.

The indicator lamps may denote the state indicating that the IV bag is at temperature and should be used next by a second intensity modulation of the indicator lamp at a frequency higher than the first intensity modulation and wherein the second intensity modulation is a discontinuous variation in intensity.

It is thus a feature of at least one embodiment of the invention to provide an intuitive signal indicating an imperative use by a blinking action.

The indicator lamps may further provide a indication that the IV bag is at temperature and expired and should not be used.

It is thus a feature of at least one embodiment of the invention to monitor total heating time of the IV bags to ensure freshness of the contents.

The indicator lamps may direct light into the IV bags on the shelves to provide a diffusion of that light through the IV bags so that diffused light is the source of indication to the user.

It is thus a feature of at least one embodiment of the invention to enlist the IV bag as a large area indicator that is both easy to see and immediately associates the state signal with the corresponding IV bag preventing confusion.

The warming cabinet door may provide a glass panel for viewing of the heating cavity when the door is closed and the indicator lamps are positioned to direct light into the IV bags laterally so that diffused light is viewed transversely through the glass panel by a user of the warming cabinet.

It is thus a feature of at least one embodiment of the invention to arrange the indicator lamps to promote the visibility of diffused lamp light rather than direct lamp light.

The compartments may be arranged in at least two columns separated by a central divider and wherein the indicator lamps are positioned in the central divider to face outward therefrom.

It is thus a feature of at least one embodiment of the invention to provide a simple method of associating indicator lamps with each compartment through a central divider which may hold the lamps and wiring associated with two columns of compartments.

The controller may determine a temperature of the IV bags by monitoring the temperature of the circulated air and modeling a heat flow into the IV bags based on a time when the IV bag was introduced into the compartment.

It is thus a feature of at least one embodiment of the invention to eliminate the need for direct temperature sensing of each IV bag which can be difficult and inaccurate in favor of a modeling process making use of the uniform thermal field. By employing a uniform thermal field, variations in compartment temperature by individual heaters and the necessary sensing of those varying temperatures is avoided. The modeling can be brought into implementation through time or temperature based measurement, both intended to correct for environmental and daily use factors.

The controller may determine an order of desired use of the IV bags by monitoring the relative times when the IV bags reach the predetermined temperature.

It is thus a feature of at least one embodiment of the invention to use the monitoring of insertion of the IV bags into the cabinet and their temperature determination to be used to efficiently cue use of the IV bags for minimizing waste.

The controller may determine an expiration time of a bag by monitoring the time when the IV bag was introduced into the compartment and comparing that time to a current time.

It is thus a feature of at least one embodiment of the invention to make use of the sensing used for bag state determination to also monitor bags for expiration. These particular objects and advantages may apply to only some embodiments falling within the claims and thus do not define the scope of the invention.

DETAILED DESCRIPTION OF THE PREFERRED EMBODIMENT

Figure 1:
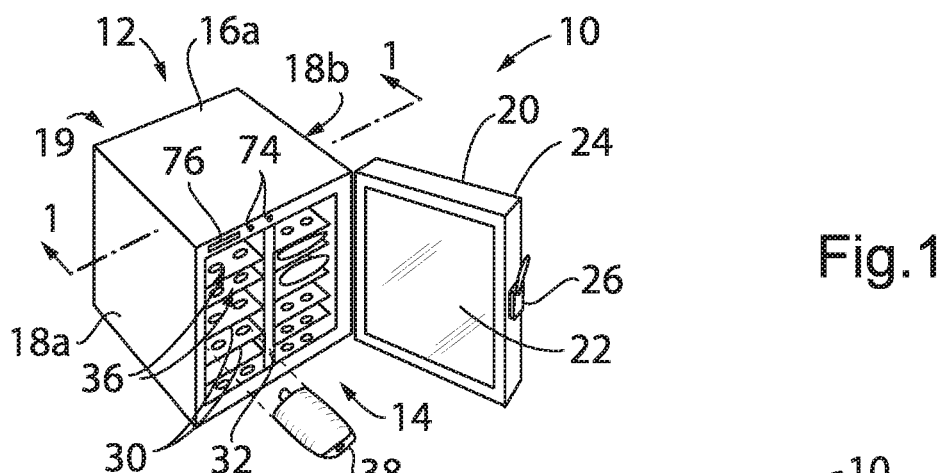
FIG. 1 is a perspective view of a heating cabinet according to the present invention showing multiple compartments for holding IV bags and for providing free exchange of air therethrough.

Referring now to FIG. 1, a thermal field IV bag warmer 10 may provide for a cabinet 12 providing a heating volume 14. The heating volume 14 is defined by upper and lower walls 16a and 16b joined by upstanding left and right walls 18a and 18b and upstanding rear wall 19, the latter enclosing a rear surface of the cabinet 12. A front surface of the cabinet 12 may be hingably attached to a door 20, for example, having a glass panel 22, which may be opened for access to the volume 14 or closed to contain heat within the heating volume 14 while still allowing viewing of the heating volume. The door 20 may have a gasketing 24 providing improved sealing when closed against the cabinet 12 and a latch and door handle 26 of standard design retaining the door 20 in the closed state or allowing it to be releasably opened as operated by a user.

The heating volume 14 may be subdivided by a set of horizontal shelves 30 arranged in left and right columns separated by a vertically extending central divider 32. Each of the shelves 30 may be perforated by openings 34 to promote airflow vertically therethrough. In one embodiment, at least 25 percent of the shelf area defined by the shelf perimeter is occupied by openings 34. In one embodiment, seven shelves 30 may be arranged in each column defining twelve compartments 36 arranged in six rows so that each compartment 36 may hold an IV bag 38 with the IV bag 38 placed with its broadest face against one shelf 30.

Figure 2:
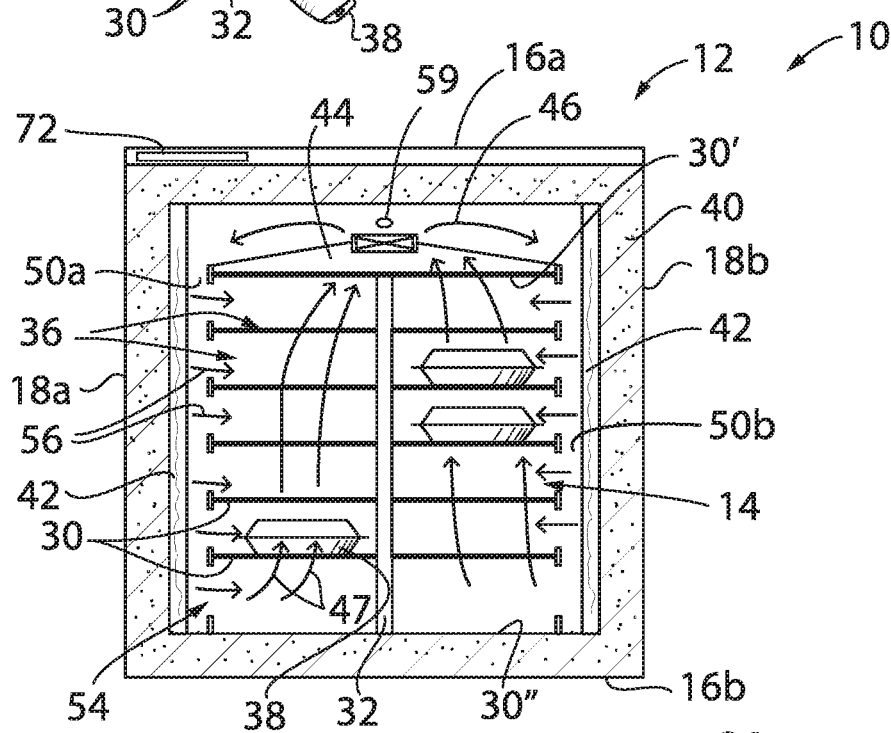
FIG. 2 is a front elevational cross-section through the cabinet of FIG. 1 along line 1-1 showing broad area high wattage heaters and a fan for circulation of air to create a uniform thermal field and showing the flow of air through the compartments holding IV bags.

Referring now to FIG. 2, thermal insulation 40 such as an air entrapping foam or batting material, such as closed-cell extruded polystyrene foam (XPS), for example, sold under the brand name Styrofoam™, or fiberglass or the like, may line the inside of the cabinet 12 adjacent to the walls 16, 18, and 19 to retain heat within the heated volume 14. Positioned inside the thermal insulation 40 of the left wall 18a and right wall 18b are heating pads 42 providing a broad area of heating commensurate with the height and depth of the assembled compartments 36. Each of the heating pads 42 may be of standard construction, for example, making use of an electrically resistive thermal cable winding through the heating pad 42 or a resistive film etched in a serpentine pattern, or other similar techniques.

An uppermost shelf 30' may open into a plenum 44 leading to a fan 46 which draws air upward through the various compartments 36 as indicated by arrows 47. This air is then conducted down left vertical distribution manifolds 50a and right vertical distribution manifolds 50b extending along respective heating pads 42 to receive heat from the heating pads 42 over substantially the entire area of the heating pads 42. The distribution manifolds 50a and 50b may flank the shelves 30 and have openings 54 leading from the manifolds 50 to each of the compartments 36 to provide airflow indicated by arrows 56 into those compartments 36. The relative size of the openings 54 may be adjusted to promote sharing of airflow and heat among the various compartments 36.

A central thermal sensor 59 may be positioned in the airflow from the fan 46 to measure the temperature of that air to approximate the temperature of the thermal field of the IV bag warmer 10. The thermal sensor 59 may be a thermocouple, resistive element, or solid-state sensor or the like.

The bottommost shelf 30" may also provide for airflow therethrough from a continuation of the manifolds 50, but in the preferred embodiment such airflow is not required based on empirical measurements.

Figure 3:
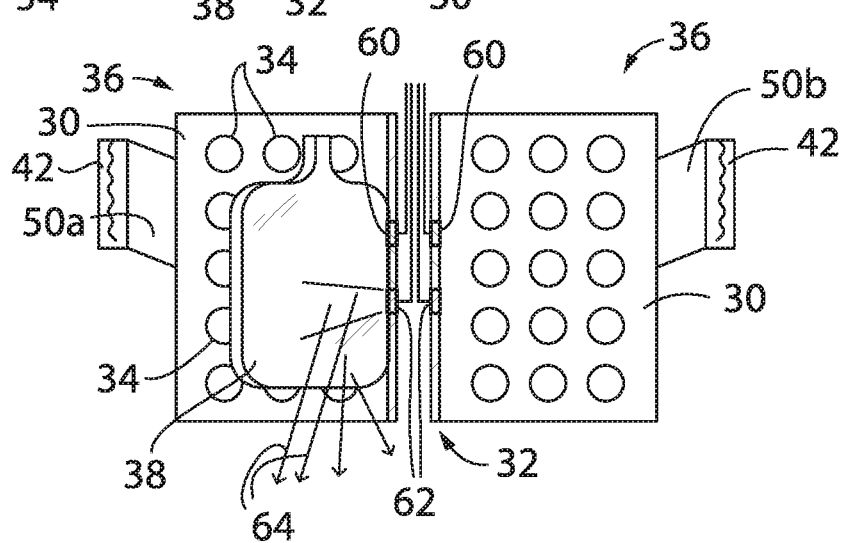
FIG. 3 is a top plan view of the shelf surface of two adjacent compartments of FIG. 1 in FIG. 2 showing the relative sizing of the compartments with respect to the IV bags to promote airflow around the IV bags and the positioning of the IV bags next to a center divider wall where presence sensors and indicator lights can be located.

Referring now to FIG. 3, each shelf 30 of each compartment 36 is sized to be larger than the resting area of an IV bag 38 so as to provide ample airflow around the IV bags 38 to heat the IV bag 38 from all sides rather than strictly from a bottom surface in contact with the shelf 30. This broad area of heating provides a lower effective thermal resistance to the contents of the IV bags 38 and more uniform heating within the IV bags 38.

The central divider 32 positioned between shelves 30 on each row may hold a proximity sensor 60 facing outward left and right into an adjacent compartment 36 to sense the presence of the IV bag 38 in the compartment 36. The sensor, for example, may be any type of proximity sensor including mechanical switch, a capacitive sensor, an infrared reflective sensor, or other sensors known in the art.

The central divider 32 may also provide LED lamps 62 facing outward left and right into each compartment 36 to project light 64 into the IV bag 38 where it is diffused to turn the IV bag into a large area indicator that glows when the LED lamp 62 is activated. This arrangement provides a signaling device that both is easily visible because of the large size of the IV bags 38 compared to a typical LED and clearly indicates the IV bag 38 associated with the signal by superimposing the signal on the relevant IV bag 38. As will be discussed below, the LEDs may be modulated to indicate the state of the IV bag 38, for example, as warming or being fully warmed, and to indicate a preferred order of using the IV bags 38 (by indicating the next IV bag 38 for use), and to indicate those IV bags 38 that have expired and should be discarded.

The shelves 30 may be a powder coated metal such as promotes conduction from the surrounding air to the IV bags 38 but generally need not be highly thermally conductive and thus in some embodiments may be a polymer material. Because the shelves 30 do not contain heaters or sensors, they may be quite thin providing good utilization of the cabinet volume and may, for example, be easily replaceable and removable for cleaning or the like.

Figure 4:
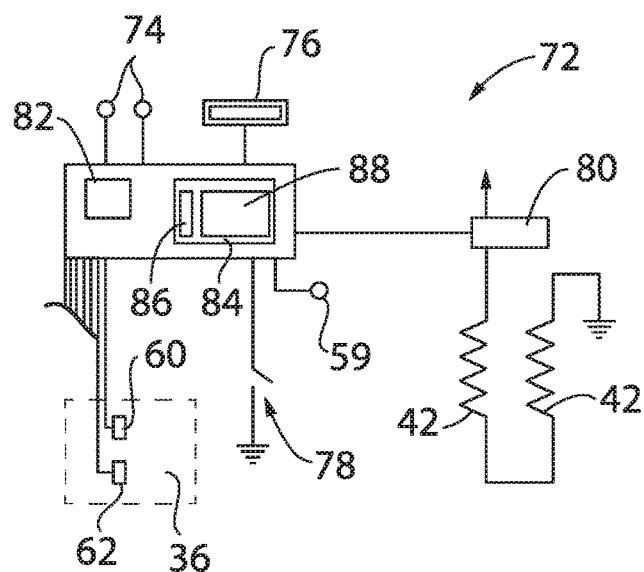
FIG. 4 is a simplified block diagram of the control electronics of the cabinets of FIG. 1 showing the computer for receiving proximity signals from each compartment and providing an indicator light in each compartment as well as a receiving signal from a temperature sensor and door switch and providing signals controlling the high wattage heaters.

Referring now to FIGS. 2 and 4, a controller 72 may be located in the cabinet 12 to communicate with controls 74, such as switches or the like, and a display 76 such as an LED seven segment display, that may be accessible to the user at the front of the cabinet 12 (for example, as shown in FIG. 1).

These control 74 and display 76 provide an interface between the user and the IV bag warmer 10 allowing entry of parameters such as a desired temperature of the uniform thermal field, the type of IV bags 38 being heated (e.g., volume), while the display 76 provides for information such as the current thermal field temperature and standard error codes and the like.

The current temperature of the thermal field of the IV bag warmer 10 may be determined by the temperature sensor 59 discussed above communicating with the controller 72. The controller 72 may also communicate with a door switch 78 indicating whether the door 20 is open or closed and with the proximity sensors 60 and LEDs 62 of each compartment 36 and with a solid-state relay 80 providing high amperage control of the heating pads 42.

The controller 72 may include a processor 82 communicating with a memory 84 holding non-transitory state data 86 and a non-transitory operating program 88. Generally, the data 86 will be information entered by the user, for example, providing for temperature setpoint, IV bag volume information, log files indicating maintenance, error codes, and the like. The program 88 provides operating instructions to perform two primary functions. The first function is to control the air temperature measured by sensor 59 to closely approximate a predetermined set point (e.g., standard body temperature) by switching on and off solid-state relay 80. The second part of the program estimates the temperature of each IV bag 38 based on a modeling process and uses estimated temperature to control the indicator lamps 62 appropriately.

Figure 5:
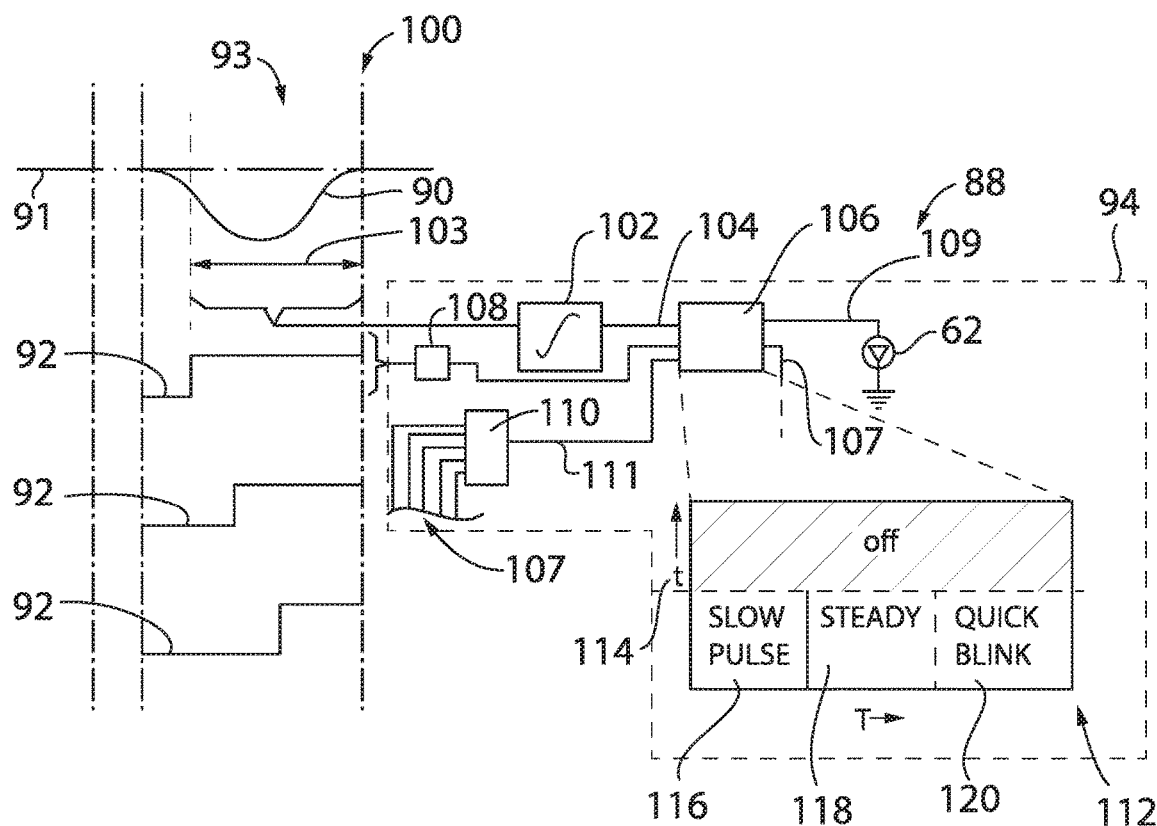
FIG. 5 is a diagrammatic representation of a program implemented by the control electronics FIG. 1 to model bag temperature without direct measurement and to provide indicator signals to a user.

Referring now to FIG. 5, in one embodiment, the operating program 88 may receive and store temperature information from the sensor 59 shown in a temperature history 90 at regular intervals in time to create a temperature history. Generally, the temperature signal will be close to a set point temperature 91; however, when the door 20 is opened, for example, at time 93 there may be a temperature drop caused by the introduction of a cool IV bag 38 into a compartment 36 and the opening of the door 20 which allows the escape of heat. Over time this temperature drop will be corrected through the addition of heat from the blanket heating pads 42.

The operating program 88 may further receive compartment proximity sensor signals 92 from each compartment 36 indicating whether an IV bag 38 is present as indicated in the figure by a high signal state. Upon receiving an indication that a given compartment 36 contains an IV bag 38, the operating program 88 instantiates a thermal model 94 for that compartment to calculate a bag state of the IV bag 38 on a regular basis.

Generally, the temperature of each IV bag 38 is modeled to eliminate the need for direct measurement of bag temperature using multiple thermal sensors or the like and eliminating the problems of making such measurements which tend to favor surface temperatures rather than temperatures deeper in the IV bags 38. In the simplest form, a modeling may make assumptions about initial bag temperatures, volumes, and the temperature of the thermal field to provide a time value indicating a time at which a given IV bag 38 can be assumed to be fully warmed.

Alternatively, the modeling may be more sophisticated taking into account fluctuations of the thermal field which can occur when the door 20 of the warming oven is opened or when multiple refrigerated IV bags 38 are introduced into the heated volume 14.

Using such a control system, at each given time 100, the thermal model 94 may review the temperature history 90 for the uniform thermal field during an interval 103 since the IV bag 38 was introduced into the compartment 36 indicated by signal 92 from a proximity sensor 59, up until the given time 100. Heat flow into the IV bag 38 may be modeled by step integrator 102 at discrete intervals based on empirically derived thermal resistance between the liquid of the IV bag 38 and the airflow surrounding the IV bag 38. This thermal resistance is applied to an imputed temperature difference between the liquid of the IV bag 38 at a temperature determined from the previous step and current temperature of the uniform thermal field from the temperature history 90 to provide a calculated heat flow into or out of the IV bag 38. The imputed heat flows in each interval are summed over the interval 103 to determine a total heat flow. This total heat flow may be applied to the known specific heat of the material of the IV bag 38 (mostly water) and mass of a standard IV bag 38 to deduce the current modeled temperature value 104 for each IV bag 38 in each compartment 36. The IV bag 38 temperature may be initially assumed to be that of a standard refrigerator equal to 59 degrees Fahrenheit. Minor errors in this assumption, will naturally be reduced over time as the calculation converges to the set point temperature 91.

It will be appreciated that the temperature history 90 may also be introduced or estimated based on the number of new refrigerated IV bags 38 introduced into the heating volume 14 and/or this measure may be used to augment the temperature signal from temperature sensor 59.

This temperature value 104 is received by a state calculator 106 together with the value of a timer 108 measuring the time duration from the insertion of the IV bag 38 into the compartment. The state calculator 106 may also receive a priority time value 111 from a comparator 110 which monitors the output of the state calculators 106 with respect to other thermal models 94 associated with different compartments 36 which will be used to deduce which IV bags 38 have reached the proper use temperature first so as to enforce an ordering of the IV bags 38 to prevent some IV bags 38 from being overlooked and thus expiring wastefully.

Referring still to FIG. 5, the state calculator 106 may consider a state space 112 having dimensions of time and temperature. After a predetermined expiration time 114, for example, on the order of six months or as short as 119 days, the state signal 107 of the state calculator 106 indicates that the IV bag 38 has expired and sends a corresponding modulation signal 109 to the LED lamp 62 associated with the compartment 36 which will turn the LEDs 62 off.

For times before the expiration time 114, the deduced temperature 104 and the priority time value 111 will be used to create one of three different state signals 107 (used by other thermal models 94) and corresponding modulation signals 109 (used by the LEDs 62). A first state 116 will provide a slowly varying modulation signal 109 (for example, following a sine wave with the frequency of 0.5 Hz) controlling the light intensity of the associated LED 62. This slowly varying modulation indicates a heating in process also indicated by state signal 107. The state 116 will be the state that the IV bag 38 enters initially in upon insertion into the IV bag warmer 10, and the state will continue until the calculated temperature 104 rises to within a predetermined tolerance of the set point temperature 91 (typically less than plus or minus 3 F around normal body temperature).

After the desired temperature has been reached, the state calculator 106 moves to state 118 outputting a state signal 107 indicating that the IV bag 38 is suitably warm for use and providing a steady modulation signal 109 for constant illumination of the LED 62. Alternatively, when the proper temperature has been reached, if the current IV bag 38 is the first IV bag 38 of those IV bags 38 to reach that desired use temperature, the state calculator 106 provides a state signal 107 providing a state 120 indicated that the IV bag 38 should be used next providing a modulation signal 109 providing a quick pulse (for example, a 3 Hz square wave). By indicating that this IV bag 38 should be used next, proper sequencing and reduced waste of available IV bags 38 is provided.

Desirably the modulation signal 109 may provide an illumination pattern of the lamp 62 recognizable and properly interpreted by those without full color vision, although the invention contemplates that any signaling type may be used.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words means for or step for are explicitly used in the particular claim.

What we claim is:

1. A warming cabinet for IV bags holding liquid medicament comprising:

a housing providing a heating cavity with a door movable between a closed state covering the heating cavity and an open state allowing access to the heating cavity;

a blower for circulating air through the heating cavity;

a set of shelves dividing the heating cavity into compartments each sized to receive an IV bag of the IV bags to be warmed, the compartments providing air passageways therebetween to receive the circulated air along paths through the compartments;

an electrical heater positioned within the circulated air for heating the circulated air;

a control unit controlling the electrical heater and executing a stored program to model a temperature of the IV bags and based on the modeling indicating particular IV bags of the IV bags that are warmed and ready for use; and visual indicators associated with each compartment of the compartments wherein the visual indicators of each compartment are independently controlled with respect to the visual indicators of the other compartments to indicate a warming state of an IV bag within the compartment based on a model of temperature of the circulated air and an elapsed time of the IV bag within the compartment, the model of temperature of the circulated air and the elapsed time of the IV bag within the compartment varying between different compartments.

2. The warming cabinet of claim 1 wherein the control unit controls the temperature of the circulated air to a temperature of a human body plus or minus five degrees Fahrenheit.

3. The warming cabinet of claim 2 wherein heat from the electrical heater communicates with the IV bags primarily through convection of the circulated air rather than conduction.

4. The warming cabinet of claim 3 wherein the shelves include a plurality of openings allowing air passage through IV bag-supporting surfaces of the shelves and wherein the openings occupy at least twenty percent of a shelf area and wherein the shelves are larger in area than a resting area of the IV bags by at least twenty-five percent.

5. The warming cabinet of claim 1 further including a manifold for distributing air from the blower to each compartment of the compartments; wherein the manifold provides vertical channels extending along opposite sides of the compartments and passing along a surface of the electrical heater.

6. The warming cabinet of claim 1 further providing a proximity sensor associated with each compartment of the compartments detecting a presence of an IV bag of the IV bags in each compartment of the compartments and wherein the compartments are arranged in at least two columns separated by a central divider and wherein the proximity sensors are positioned in the central divider to face outward therefrom.

7. The warming cabinet of claim 1 wherein the control unit determines a temperature of each IV bag of the IV bags based on a modeling of the temperature of each IV bag of the IV bags without measurement of the temperature of each IV bag of the IV bags.

8. The warming cabinet of claim 7 wherein the control unit determines the temperature of each IV bag of the IV bags based on at least one of a monitoring of the temperature of the circulated air and times of introductions of the IV bags into the compartments.

9. The warming cabinet of claim 1 wherein the control unit determines an expiration time of the IV bags by monitoring a time when the IV bags were introduced into the compartments and comparing the time to a current time.

10. A warming cabinet for IV bags holding liquid medicament comprising:
a housing providing a heating cavity with a door movable between a closed state covering the heating cavity and an open state allowing access to the heating cavity;
a blower for circulating air through the heating cavity;
a set of shelves dividing the heating cavity into compartments each sized to receive an IV bag of the IV bags to be warmed, the compartments providing air passageways therebetween to receive the circulated air along paths through the compartments;
an electrical heater positioned within the circulated air for heating the circulated air;
a control unit controlling the electrical heater and executing a stored program to model a temperature of the IV bags and based on the modeling indicating particular IV bags of the IV bags that are warmed and ready for use; and
a set of indicator lamps attached to an inner wall within each compartment of the compartments and directed into the compartments to illuminate the compartment and contents of the compartment thereby indicating states of the IV bags with respect to heating of the IV bags, including a state indicating that the IV bags are heating and not at a predetermined desired temperature and a state indicating that the IV bags are at the predetermined desired temperature.

11. The warming cabinet of claim 10 wherein the indicator lamps denote the state indicating that the IV bags are heating and not at the predetermined desired temperature by a predetermined first intensity modulation of the indicator lamps changing an intensity of the indicator lamps and denote the state indicating that the IV bags are at the predetermined desired temperature with a steady illumination of the indicator lamps.

12. The warming cabinet of claim 11 wherein the predetermined first intensity modulation provides a continuous variation in intensity.

13. The warming cabinet of claim 11 further wherein the indicator lamps further indicate a state denoting that the IV bags are at the predetermined desired temperature and should be used next.

14. The warming cabinet of claim 13 wherein the indicator lamps denote the state indicating that the IV bags are at the predetermined desired temperature and should be used next by means of a predetermined second intensity modulation of the indicator lamps at a frequency higher than the predetermined first intensity modulation and wherein the predetermined second intensity modulation is a discontinuous variation in intensity.

15. The warming cabinet of claim 10 further including a state indicating that the IV bags are at the predetermined desired temperature and expired and should not be used.

16. The warming cabinet of claim 10 wherein the indicator lamps associated with each compartment of the compartments for indicating a state of the IV bags with respect to heating of the IV bags direct light toward the IV bags on each shelf and into the IV bags on the shelves to provide a diffusion of the light through the IV bags so the diffused light provides the indication that the particular IV bags are warmed and ready for use.

17. The warming cabinet of claim 16 wherein the door provides a glass panel for viewing of the heating cavity when the door is closed and the indicator lamps are positioned to direct the light into the IV bags laterally so the diffused light is viewed transversely through the glass panel by a user of the warming cabinet.

18. The warming cabinet of claim 16 wherein the compartments are arranged in at least two columns separated by a central divider and wherein the indicator lamps are positioned in the central divider to face outward therefrom.

19. A warming cabinet for IV bags holding liquid medicament comprising:
a housing providing a heating cavity with a door movable between a closed state covering the heating cavity and an open state allowing access to the heating cavity;
a blower for circulating air through the heating cavity;
a set of shelves dividing the heating cavity into compartments each sized to receive an IV bag of the IV bags to be warmed, the compartments providing air passageways therebetween to receive the circulated air along paths through the compartments;
an electrical heater positioned within the circulated air for heating the circulated air;
a control unit controlling the electrical heater and executing a stored program to model a temperature of the IV bags and based on the modeling indicating particular IV bags of the IV bags that are warmed and ready for use; and
visual indicators associated with each compartment of the compartments;
wherein the control unit determines an order of desired use of the IV bags by monitoring relative times when the IV bags reach a predetermined desired temperature, the predetermined desired temperature determined without direct temperature measurement of the IV bag to indicate the order of desired use through the visual indicators prioritizing among IV bags that have reached the predetermined desired temperature.

20. A warming cabinet for IV bags holding liquid medicament comprising:
a housing providing a heating cavity with a door movable between a closed state covering the heating cavity and an open state allowing access to the heating cavity;
a set of shelves dividing the heating cavity into compartments each sized to receive an IV bag of the IV bags to be warmed;
at least one electrical heater positioned to apply heat to the compartments to heat the IV bags;
a set of visual indicators attached to an inner wall within each compartment and positioned in each of the compartments to contact the IV bags to illuminate the IV bags through internal diffusion within the IV bags; and
a control unit executing a stored program to independently indicate a status of each IV bag with respect to heating of the IV bags through activation of a corresponding visual indicator of the set of visual indicators based on a model of temperature of circulated air through the heating cavity and an elapsed time of the IV bag within the compartment, the model varying between different compartments.

* * * * *